United States Patent
Ardilouze et al.

(10) Patent No.: US 12,329,762 B2
(45) Date of Patent: Jun. 17, 2025

(54) PHARMACEUTICAL PREPARATION FOR IMPROVING ABSORPTION AND POSTPRANDIAL HYPOGLYCEMIC ACTION OF INSULIN

(71) Applicant: Eli Lilly and Company, Indianapolis, IN (US)

(72) Inventors: Jean-Luc Ardilouze, Sherbrooke (CA); Maude Gagnon-Auger, Sherbrooke (CA); Fernand Gobeil, Sherbrooke (CA); Julie Menard, Sherbrooke (CA); Jean-Patrice Baillargeon, Sherbrooke (CA); Pascal Brassard, Magog (CA)

(73) Assignee: ELI LILLY AND COMPANY, Indianapolis, IN (US)

(*) Notice: Subject to any disclaimer, the term of this patent is extended or adjusted under 35 U.S.C. 154(b) by 0 days.

(21) Appl. No.: 18/156,633

(22) Filed: Jan. 19, 2023

(65) Prior Publication Data

US 2023/0158043 A1    May 25, 2023

Related U.S. Application Data

(63) Continuation of application No. 15/747,532, filed as application No. PCT/CA2016/050886 on Jul. 28, 2016, now abandoned.

(60) Provisional application No. 62/197,833, filed on Jul. 28, 2015.

(51) Int. Cl.
| | |
|---|---|
| *A61K 31/5578* | (2006.01) |
| *A61K 9/00* | (2006.01) |
| *A61K 31/137* | (2006.01) |
| *A61K 31/472* | (2006.01) |
| *A61K 31/519* | (2006.01) |
| *A61K 31/557* | (2006.01) |
| *A61K 31/5585* | (2006.01) |
| *A61K 38/28* | (2006.01) |
| *A61K 45/06* | (2006.01) |
| *A61P 3/10* | (2006.01) |
| *C07D 215/20* | (2006.01) |
| *C07D 217/20* | (2006.01) |
| *C07D 487/04* | (2006.01) |
| *C07K 14/62* | (2006.01) |

(52) U.S. Cl.
CPC ........ *A61K 31/5578* (2013.01); *A61K 9/0019* (2013.01); *A61K 31/137* (2013.01); *A61K 31/472* (2013.01); *A61K 31/519* (2013.01); *A61K 31/557* (2013.01); *A61K 31/5585* (2013.01); *A61K 38/28* (2013.01); *A61K 45/06* (2013.01); *A61P 3/10* (2018.01); *C07D 215/20* (2013.01); *C07D 217/20* (2013.01); *C07D 487/04* (2013.01); *C07K 14/62* (2013.01)

(58) Field of Classification Search
None
See application file for complete search history.

(56) References Cited

U.S. PATENT DOCUMENTS

| | | | |
|---|---|---|---|
| 5,981,594 | A | 11/1999 | Okamoto et al. |
| 8,324,157 | B2 | 12/2012 | Olsen et al. |
| 2005/0282903 | A1 | 12/2005 | Wade et al. |
| 2015/0065423 | A1 | 3/2015 | Laulicht et al. |

FOREIGN PATENT DOCUMENTS

| | | | |
|---|---|---|---|
| CA | 2415392 A1 | 1/2002 | |
| CA | 2584095 A1 | 4/2006 | |
| EP | 0001124 A1 | 3/1979 | |
| EP | 2500020 A1 | 9/2014 | |
| WO | 2003094956 A1 | 11/2003 | |
| WO | 2010023666 A2 | 3/2010 | |
| WO | 2010149772 A1 | 12/2010 | |
| WO | 2012080362 A1 | 6/2012 | |
| WO | 2015120457 A1 | 8/2015 | |
| WO | WO-2015171484 A1 * | 11/2015 | ........... A61K 31/192 |
| WO | 2016177660 A1 | 11/2016 | |

OTHER PUBLICATIONS

Paolisso et al. "Low-Dose Iloprost Infusion Improves Insulin Action in Aged Healthy Subject and NIDDM Patients" Diabetes Care 18:200-205. (Year: 1995).*
Sato et al. "The Prostacyclin Analog Beraprost Sodium Ameliorates Characteristics of Metabolic Syndrome in Obese Zucker (Fatty) Rats" Diabetes 59:1092-1100. (Year: 2010).*
Anonymous "Diabetes treatment: Medications for type 2 diabetes" Mayo Clinic, https://www.mayoclinic.org/diseases-conditions/type-2-diabetes/in-depth/diabetes-treatment/art-20051004. (Year: 2005).*
Gotzsche, O. (1985). Acute insulin treatment normalizes the resistance to the cardiotoxic effect of isoproterenol in streptozotocin diabetic rats. A morphometric study of isoproterenol induced myocardial fibrosis. *Virchows Archiv. A, Pathological anatomy and histology*, 405(2), 193-201.
Fernandez, M., et al. (2008). Addition of pioglitazone and ramipril to intensive insulin therapy in type 2 diabetic patients improves vascular dysfunction by different mechanisms. *Diabetes Care*, 31(1), 121-127.
Emerich, D. F., Dean, R. L., Osborn, C., & Bartus, R. T. (2001). The development of the bradykinin agonist Labradimil as a means to increase the permeability of the blood-brain barrier. *Clinical pharmacokinetics*, 40(2), 105-123.
American Diabetes Association. (2015). 7. Approaches to glycemic treatment. *Diabetes care*, 38(Suppl 1):S41-48.

(Continued)

*Primary Examiner* — Sudhakar Katakam
*Assistant Examiner* — Zachary J Miknis
(74) *Attorney, Agent, or Firm* — Perry Woo (57) ABSTRACT

The present disclosure relates to compositions and combinations comprising one or more insulin(s) and one or more vasoactive agent(s), and use thereof for increasing subcutaneous insulin absorption and/or treating diabetes and/or treating or preventing hyperglycemia or complications in a patient in need thereof.

8 Claims, 9 Drawing Sheets

(56) References Cited

OTHER PUBLICATIONS

Gagnon-Auger, M., du Souich, P., Baillargeon, J. P., Martin, É., Brassard, P., Ménard, J., & Ardilouze, J. L. (2010). Dose-dependent delay of the hypoglycemic effect of short-acting insulin analogues in obese subjects with type 2 diabetes mellitus: a pharmacokinetic and pharmacodynamic study. *Diabetes Care*.

Karpe, F., Fielding, B. A., Ardilouze, J. L., Ilic, V., Macdonald, I. A., & Frayn, K. N. (2002). Effects of insulin on adipose tissue blood flow in man. *The Journal of physiology*, 540(3), 1087-1093.

Takatori, S., Mizote, M., Zamami, Y., Kurosaki, Y., & Kawasaki, H. (2003). Effects of insulin on vascular responses to spinal cord stimulation and vasoactive agents in pithed rats. *British journal of pharmacology*, 140(6), 1137-1145.

Lin, C. S., Lin, G., Xin, Z. C., & Lue, T. F. (2006). Expression, distribution and regulation of phosphodiesterase 5. *Current pharmaceutical design*, 12(27), 3439-3457.

American Diabetes Association. (2015). 6. Glycemic Targets. *Diabetes care*, 38(Suppl 1):S33-40.

Sandilands, E. A., et al. (2013). Histamine-induced vasodilatation in the human forearm vasculature. *British journal of clinical pharmacology*, 76(5), 699-707.

Vanhoutte, P. M. (2009). How we learned to say No. *Arteriosclerosis, thrombosis, and vascular biology*, 29(8), 1156-1160.

Hirsch, I. B. (2005). Insulin analogues. *New England Journal of Medicine*, 352(2), 174-183.

Sotornik, R., & Ardilouze, J. L. (2014). Measurement and manipulation of human adipose tissue blood flow using xenon washout technique and adipose tissue microinfusion. In *Methods in enzymology* (vol. 537, pp. 227-242). Academic Press.

Pedersen, K. E., Buckner, C. K., Meeker, S. N., & Undem, B. J. (2000), Pharmacological examination of the neurokinin-1 receptor mediating relaxation of human intralobar pulmonary artery. *Journal of Pharmacology and Experimental Therapeutics*, 292(1), 319-325.

Sandhiya, S., & Dkhar, S. A. (2009). Potassium channels in health, disease & development of channel modulators. *Indian Journal of Medical Research*, 129(3), 223.

Duthois, S., Cailleux, N., Benosman, B., & Levesque, H. (2003). Tolerance of Iloprost and results of treatment of chronic severe lower limb ischaemia in diabetic patients. A retrospective study of 64 consecutive cases. *Diabetes & metabolism*, 29(1), 36-43.

Ghimire, G., Hage, F. G., Heo, J., & Iskandrian, A. E. (2013). Regadenoson: a focused update. *Journal of Nuclear Cardiology*, 20(2), 284-288.

Martin, E., Brassard, P., Gagnon-Auger, M., Yale, P., Carpentier, A. C., & Ardilouze, J. L. (2011). Subcutaneous adipose tissue metabolism and pharmacology: a new investigative technique. *Canadian journal of physiology and pharmacology*, 89(6), 383-391.

Blaise, S., et al., "Cathodal Iontophoresis of Treprostinil Induces a Sustained Increase in Cutaneous Blood Flux in Healthy Volunteers," J. Clin. Pharmacol., vol. 53, Issue 1, pp. 58-66 (2012).

Gille, A., et al., "Nicotinic Acid: Pharmacological Effects and Mechanisms of Action," Annu. Rev. Pharmacol. Toxicol., vol. 48, pp. 79-106 (2008).

Mathier, M., et al., "Subcutaneous Treprostinil in Pulmonary Arterial Hypertension: Practical Considerations," J. Heart Lung Transplant., vol. 29, pp. 1210-1217 (2010).

McSwain, C., et al., "Dose Proportionality of Treprostinil Sodium Administered by Continuous Subcutaneous and Intravenous Infusion," J. Clin. Pharmacol., vol. 48, pp. 19-25 (2008).

Menon, R., et al., "Insulin Absorption Accelerated by a-Adrenergic Blockade at Injection Site," Diabetes Care, vol. 10, No. 4, pp. 470-472 (1987).

Moriarty, R., et al., "The Intramolecular Asymmetric Pauson-Khand Cyclization as a Novel and General Stereoselective Route to Benzindene Prostacyclins: Synthesis of UT-15 (Treprostinil)," J. Org. Chem, vol. 69, pp. 1890-1902 (2004).

Owens, D., et al., "The Influence of Aprotinin on Regional Absorption of Soluble Human Insulin," Br. J. Clin. Pharmac., vol. 25, pp. 453-456 (1988).

Vora, J., et al., "Relationship Between Absorption of Radiolabeled Soluble Insulin, Subcutaneous Blood Flow, and Anthropometry," Diabetes Care, vol. 15, No. 11, pp. 1484-1493 (1992).

Wade, M., et al., "Absolute Bioavailability and Pharmacokinetics of Treprostinil Sodium Administered by Acute Subcutaneous Infusion," J. Clin. Pharmacol., vol. 44, pp. 83-88 (2004).

Williams, G., et al., "Subcutaneous Aprotinin Causes Local Hyperaemia," Diabetologia, vol. 24, pp. 91-94 (1983).

Williams, G., et al., "Prostaglandin E1 Accelerates Subcutaneous Insulin Absorption in Insulin-Dependent Diabetic Patients," Diabetic Medicine, pp. 109-113 (1984).

NDA 21-272, RemodulinTM, Medical Review, available at http://www.accessdata.ida.gov/drugsatda_docs/nda/2002/21-272_Remodulin.cfm, pp. 1-195, (Jul. 31, 2002).

NDA 21-272, RemodulinTM, Clinical Pharmacology & Biopharmaceutics Review(s), available at http://www.accessdat.fda.gov/drugsatfda_docs/nda/d002/21-272_Pemodulin.cfm, pp. 1-112, (Jul. 31, 2002).

Remodulin® (treprostinil) Injection Package Insert, pp. 1-17, (May 2002).

Heart View, vol. 17, No. 4, p. 53(385)-60(392), 2013.

Skoro-Sajer, Nika, et al., "Treprostinil for Pulmonary Hypertension," Vascular Health and Risk Management, Jan. 1, 2008, pp. 507-513.

B.J.Whittle, et al., "Binding and activity of the prostacyclin receptor (IP) agonists, treprostinil and iloprost, at human prostanoid receptors: Treprostinil is a potent $DP_1$ and $EP_2$ agonist," Biochemical Pharmacology, 84 (2012) 68-75.

Paolisso, G., Di Maro, G., D'amore, A., Passariello, N., Gambardella, A., Varricchio, M., & D'onofrio, F. (1995). Low-dose iloprost infusion improves insulin action in aged healthy subjects and NIDDM patients. *Diabetes Care*, 18(2), 200-205.

Perimenis, P. et al., "Switching from Long-Term Treatment with Self-Injections to Oral Sildenafil in Diabetic Patients with Severe Erectile Dysfunction", European Urology, 2002, 41(4): 387-391.

Weber, T. et al., "Subcellular distribution and phosphorylation state of insulin receptors from insulin- and isoproterenol-treated rat adipose cells", Cellular Signaling, 1991, 3(1): 51-58.

Siebenhofer, A. et al., "Short acting insulin analogues versus regular human insulin in patients with diabetes mellitus," Cochrane Database of Systemic Reviews, 2009, 2: 1-2.

\* cited by examiner

PHARMACEUTICAL PREPARATION FOR IMPROVING ABSORPTION AND POSTPRANDIAL HYPOGLYCEMIC ACTION OF INSULIN

FIELD OF THE DISCLOSURE

The present disclosure relates to novel compositions, combinations and methods for increasing subcutaneous insulin absorption and/or treating diabetes and/or treating or preventing hyperglycemia in a patient in need thereof.

BACKGROUND OF THE DISCLOSURE

Diabetes is a chronic metabolic disease that is characterised by high glucose levels in the blood (hyperglycemia). Depending on the type of diabetes, the organism does not produce insulin (type 1) and/or has difficulty reacting to its signal (type 2). Insulin is a hormone produced by beta pancreatic cells and its secretion is mainly stimulated by an increase of glucose in the blood, but also by free fatty acids, amino acids, incretins, and other factors. Insulin controls hyperglycemia by stimulating the capting of glucose by the tissues. In other words, insulin activates energy storage and simultaneously inhibits the release of energy reserves.

Among the diabetic population, 10% of patients are of type 1 (T1D) and 90% are of type 2 (T2D).

Short-acting insulin analogues (SAIA) are widely used nowadays. Originally, they were designed to synchronize plasma insulin increase and food absorption. SAIA are indeed absorbed more quickly than regular human insulin (RHI). Insulin's physicochemical properties explain differences in absorption between RHI and SAIA. SAIA are insulins with a reduced tendency to self-associate, providing faster absorption, lesser within- and between-subjects variability and better reproducibility. Accordingly, rises in plasma and expected hypoglycemic responses are more rapid. Of note these studies were conducted in normal weight healthy subjects or in subjects with T1D; accordingly, only small dosages of insulin were assessed.

Therefore, in patients with T2D, SAIA therapy is essentially based on the pharmacokinetic (PK) and pharmacodynamic (PD) data of the above small-dosage studies conducted in subjects with T1D, normal weight or moderately obese subjects. The paradox is that 75% of all insulin users are, in fact, obese insulin-resistant patients with T2D who inject insulin or mixed insulin one to four times daily at much larger dosages (30, 60, 90 units (U) and more).

Although improvements were noted in T1D subjects, no consistent and constant improvement in glycemic control was ever observed in T2D subjects using SAIA instead of RHI. Consequently, there is still a need to improve the therapy of diabetic patients, especially with the goal of reducing the risk of heart attacks and other cardiovascular diseases, kidney failure, lower limb amputation and blindness.

SUMMARY

In an aspect of the disclosure, there is provided a method for treating diabetes comprising simultaneously administering subcutaneously to the same exact location/site in a subject in need thereof, a therapeutically effective amount of one or more insulins and a subcutaneously effective amount of one or more vasoactive agents.

In another aspect of the disclosure, there is provided a pharmaceutical composition comprising a therapeutically effective amount of one or more insulins and a subcutaneously effective amount of one or more vasoactive agents.

In another aspect of the disclosure, there is provided a combination comprising a therapeutically effective amount of one or more insulins and a subcutaneously effective amount of one or more vasoactive agents.

In another aspect of the disclosure, there is provided a method for increasing subcutaneous insulin absorption in a subject in need thereof comprising simultaneously administering subcutaneously to the same site in a subject a subcutaneously effective amount of one or more vasoactive agents and said insulin.

In an aspect of the disclosure, there is provided a method for delaying or preventing the progression of T2D or conditions related to the progression of T2D comprising simultaneously administering subcutaneously to the same site in a subject in need thereof, a therapeutically effective amount of one or more insulins and a subcutaneously effective amount of one or more vasoactive agents.

In an aspect of the disclosure, there is provided a method for the treatment or prevention of hyperglycemia comprising simultaneously administering subcutaneously to the same site in a subject in need thereof, a therapeutically effective amount of one or more insulins and a subcutaneously effective amount of one or more vasoactive agents.

DESCRIPTION OF THE EMBODIMENTS

In accordance with one embodiment, there is provided a method for treating diabetes comprising simultaneously administering subcutaneously to the same site in a subject in need thereof, a therapeutically effective amount of an insulin and a subcutaneously effective amount of one or more vasoactive agents.

In accordance with one embodiment, there is provided a method for treating diabetes comprising simultaneously administering subcutaneously to the same site in a subject in need thereof, a therapeutically effective amount of an insulin and a subcutaneously effective amount of a vasoactive agent.

In another embodiment of the disclosure, there is provided a pharmaceutical composition comprising a therapeutically effective amount of an insulin and an effective amount of one or more vasoactive agents.

In another embodiment of the disclosure, there is provided a pharmaceutical composition comprising a therapeutically effective amount of an insulin and a subcutaneously effective amount of a vasoactive agent.

In another embodiment of the disclosure, there is provided a combination comprising a therapeutically effective amount of an insulin and a subcutaneously effective amount of one or more vasoactive agents.

In another embodiment of the disclosure, there is provided a combination comprising a therapeutically effective amount of an insulin and a subcutaneously effective amount of a vasoactive agent.

In another embodiment of the disclosure, there is provided a method for increasing subcutaneous insulin absorption in a subject in need thereof comprising simultaneously administering subcutaneously to the same site in a subject a subcutaneously effective amount of a vasoactive agent and said insulin.

In an embodiment of the disclosure, there is provided a method for delaying or preventing the progression of T2D or conditions related to the progression of T2D comprising simultaneously administering to a subject in need thereof, a therapeutically effective amount of an insulin and a subcutaneously effective amount of a vasoactive agent.

In an embodiment of the disclosure, there is provided a method for the treatment or prevention of hyperglycemia comprising simultaneously administering to a subject in need thereof, a therapeutically effective amount of an insulin and a subcutaneously effective amount of a vasoactive agent.

As used herein "simultaneous" or "simultaneously" refers to the administration of one or more vasoactive agents and one or more insulins substantially at the same time. What is understood by administration substantially at the same time is that the vasoactive agent(s) must be administered sufficiently close in time with regard to the insulin, to allow sufficient exposure time of the insulin to the local increase of subcutaneous ATBF caused by the vasoactive agents. Preferably, the administration of one or more vasoactive agents and one or more insulins is at the same time.

What is understood by administration "to the same site", is that the vasoactive agent(s) must be administered in a vicinity sufficiently close to the insulin injection site to allow an exposure of the insulin to the local increase of subcutaneous ATBF caused by the vasoactive agent(s).

In one embodiment, the vasoactive agent(s) and insulin(s) are administered as a pharmaceutical composition comprising the vasoactive agent(s) and insulin(s) (i.e. in a combined dosage form).

In one embodiment, the vasoactive agent(s) and insulin(s) are used in combination (i.e. as separate or combined formulations) and administered simultaneously. The separate formulations may be administered by separate administration devices (such as syringes and subcutaneous needles) or any device allowing the delivery of the two formulations to the same site.

In one embodiment, the one or more vasoactive agent(s) is used in combination with regular mammalian insulin(s) or any transformed (genetically or by any other means) insulin such as currently available SAIA (e.g., insulin lispro (Humalog®), insulin glulisine (Apidra®), insulin aspart (Novolog®)), and whichever the composition of excipients or dilution liquid.

In one embodiment of the methods, composition or combination described herein, said insulin is transformed insulin, preferably a short-acting insulin analogues (SAIA) such as is insulin lispro, insulin glulisine or insulin aspart. In one embodiment, the said insulin is insulin lispro.

As defined herein "patient" refers to both human and non-human subjects (e.g., dog, cat, horse, other). The subject is preferably human.

Diabetes can be divided into two broad types of diseases: T1D and T2D. T1D is caused by beta-cell destruction, usually leading to insulin deficiency. T2D (historically called non-insulin-dependent diabetes) may range from predominantly insulin resistance with relative insulin deficiency to a predominantly secretory defect with insulin resistance, leading to insulin therapy.

In one embodiment, the patient is a human T1D patient, said patient being underweight, normal weight, overweight, or obese.

In one embodiment, the patient is a human T2D patient, underweight, normal weight, overweight, or obese.

In a further embodiment, the patient is an obese human T2D patient.

Still in a further embodiment, the patient is uncontrolled T2D patient.

As used herein, "underweight" refers to an adult patient having a body mass index (BMI)<18.50 kg/m$^2$ or a child having a weight under the $5^{th}$ percentile, "normal weight" refers to an adult patient having a BMI between 18.50 and 24.99 kg/m$^2$ or a child having a weight at the $5^{th}$ percentile to less than the $85^{th}$ percentile, "overweight" refers to an adult patient having a BMI between 25.00 and 29.99 kg/m$^2$ or a child having a weight at the $85^{th}$ percentile to less than the $95^{th}$ percentile, and "obese" refers to an adult patient having a BMI≥30.00 kg/m$^2$ or a child having a weight at the $95^{th}$ percentile or greater.

As used herein "uncontrolled diabetes" refers to patient characterized by elevated levels of $A_{1c}$ (also referred to as hemoglobin $A_{1c}$, or $HbA_{1c}$).

According to the 2015 American Diabetes Association recommendations, "a reasonable $A_{1c}$ goal for many non-pregnant adults is <7%. Providers might reasonably suggest more stringent $A_{1c}$ goals, such as <6.5%, for selected individual patients if this can be achieved without significant hypoglycemia or other adverse effects of treatment. Less stringent $A_{1c}$ goals, such as <8%, may be appropriate for patients with a history of severe hypoglycemia, limited life expectancy, advanced micro- or macrovascular complications, or long-standing diabetes in whom the general goal is difficult to attain" (Diabetes Care 2015;38 Suppl:S33-S40). "If the $A_{1c}$ target is not achieved after approximately 3 months, the diabetes is considered uncontrolled with the actual therapy. In the case of patients with T1D, insulin doses will be adjusted. In regard of patients with T2D, it is suggested to the attending physician to apply the next step of the antihyperglycemic therapy recommendations. After the attempt of controlling diabetes by an intervention on patient's lifestyle (i.e. healthy eating, increased physical activity, weight control, etc.), recommended therapies are as following: monotherapy, dual therapy, triple therapy, and combination injectable therapy" (Diabetes Care 2015;38 Suppl:S41-S48). "All therapies involve oral antihyperglycemic agents and only the last one requires mealtime insulin therapy. However, in patients with newly diagnosed T2D and markedly symptomatic and/or elevated blood glucose levels or $A_{1c}$, initiating insulin therapy is recommended. More precisely, starting combination insulin therapy is to consider when $A_{1c}$ is ≥10-12%" (Diabetes Care 2015;38 Suppl: S41-S48).

As used herein, progression of T2D can be seen as the increase in glycated hemoglobin ($A1_c$) or development or worsening of complications recognized as related to diabetes—for example retinopathy, nephropathy, neuropathy, cardiovascular diseases but many other could be listed).

The term "Short Acting Insulin Analogne" or "SAIA" is understood to mean a polypeptide derived from the naturally occurring insulin, such as human insulin. The analog is typically obtained by addition and/or deletion and/or substitution and/or inversion of one or more amino acids of the naturally occurring insulin (Hirsch I B. *N Engl J Med* 2005;352(2): 174-83). SAIA are also sometimes referred to as "Rapid Acting Insulin Analog". The expressions can be used interchangeably herein.

In the present disclosure, it is contemplated that vasoactive agents for use herein should be appropriate to cause a local increase of blood flow in subcutaneous adipose tissue (ATBF), it would be desirable that the vasoactive agents: 1) is operative in diabetic patients 2) provide a sufficient stability into the subcutaneous adipose tissue in the patient and/or 3) be compatible (i.e. not detrimental) for use in patients.

ATBF was assessed using the $^{133}$Xe washout technique, the gold standard technique, as described below in Examples (Experimental protocol for Assessment of ATBF) and also in (Karpe F, et al. *J Physiol* 2002;540(Pt 3):1087-93; Martin E, et al. *Can J Physiol Pharmacol* 2011;89(6):383-91; Sotornik R, et al. *Methods Pnzymol.* 2014;537:227-42). In one embodiment, the vasoactive agents for use herein cause a local increase of ATBF that is sufficient to be detected using the $^{133}$Xe washout technique or by any other accurate methods.

An example of a suitable class of vasoactive agent includes prostacyclin $IP_1$ receptor agonists such as iloprost (Ilomedine®, Ventavis®), epoprostenol (Flolan® and Veletri®) or treprostinil (Remodulin® & Tyvaso®). The $IP_1$ receptors are known to mediate endothelium-independent dilatation of vessels, increasing blood flow in the area (Duthois S, et al. *Diabetes Metab* 2003;29(1):36-43). Other suitable classes of very powerful vasoactive agents and agonists of protein G-coupled receptors are: purinergic class 2 receptor agonists such as regadenoson (Lexiscan®), which is an adenosine $A_{2A}$ receptor agonist (Ghimire G, et al. *J Nucl. Cardiol.* 2013;20(2):284-8); tachykinin receptor agonists such as Homspera®, which is a substance P $NK_1$ receptor agonist (Pedersen K E, et al. J Pharmacol Exp. Ther 2000;292(1):319-25); histaminergic class 2 receptor agonists such as betazole, which is an histamine $H_2$ receptor agonist (Sandilands E A, et al. *Br. J Clin Pharmacol* 2013; 76(5):699-707); and kinin $B_2$ receptor agonist such as labradimil, which is a bradykinin $B_2$ receptor agonist (Emerich D F, et al. *Clin Pharmacokinet.* 2001;40(2):105-23). Another suitable class of vasoactive agents is the potassium channel openers, like minoxidil, nicorandil and maxipost (Sandhiya S, Dkhar S A. *Indian J Med Res* 2009; 129(3): 223-32).

Another efficient way to increase ATBF is to use two complementary classes of vasoactive agents such as nitrogen oxide donors class (e.g., nitroglycerin, nitroprusside, etc.) coupled to the inhibitors of cyclic guanosine monophosphate phosphodiesterases (ex: sildenafil, tadalafil, papaverine, etc.) The first vasoactive agent class increases the production of cyclic guanosine monophosphate and the second class decreases its degradation (Lin C S, et al. *Curr Pharm. Des* 2006;12(27):3439-57; Vanhoutte P M. *Arterioscler. Thromb. Vasc. Biol.* 2009;29(8):1156-60).

An additional way to increase ATBF is to use cell-permeable, non-hydrolysable analogs of cAMP (e.g., db-cAMP, 8-bromo-cAMP, Sp-5,6-DC1-cBiMPS) and cGMP (e.g., 8-p-CPT-cGMP, 8-bromo-cGMP).

In any embodiment of the methods, composition or combination described herein, said vasoactive agent is prostacyclin $IP_1$ receptor agonist, such as iloprost, epoprostenol or treprostinil; especially iloprost.

Vasoactive agents for use herein are used at dosages typically substantially lower than typical doses approved by health and medical authorities. Such dosages can be used in the present method because the vasoactive agent locally provides an immediate action where insulin is administered. At body scale the dose injected is minimal (about 9 to 140 times inferior with regard to i.v. doses) although at local site, this dose is pharmacologically active. It is believed that the use of lower doses may offer advantages such as reducing side effects normally encountered by effective systemic doses. It is also believed that subcutaneous administration reduces the bioavailability of the agents compared to the doses delivered by i.v. bolus. An example of a suitable dose of vasoactive agent ($IP_1$ receptor agonists) such as iloprost is provided in Table 1.

TABLE 1

Comparison of typical i.v. doses of iloprost and maximum subcutaneous doses used in this description.

| Vasoactive agent | Recommended intravenous (iv) doses | Recommended iv dose in a standard 70-kg patient | Our subcutaneous (sc) dose | iv/sc ratio |
|---|---|---|---|---|
| iloprost $IP_1$ receptor agonist | 0.72 µg/kg (over 6 hrs) | 50.4 µg or 140 nmol (over 6 hrs) | 1 nmol (bolus) | 140 |

In another embodiment, the dosage form of the disclosure can be adjusted by varying the amount and types of vasoactive agents for a greater effect in increasing local blood flow.

The excipient(s) for use in pharmaceutical compositions in accordance with the disclosure must be "pharmaceutically acceptable" in the sense of being compatible with the other ingredients of the formulation and not being deleterious to the recipient thereof. The pharmaceutical composition, or for instance each component of the combination, in particular the composition comprising insulin, may optionally comprise excipients such as preservatives, chelating agents, tonicity modifiers, bulking agents, stabilizers, antioxidants, polymers and surfactants, metal ions, oleaginous vehicles and proteins (e.g., human serum albumin, gelatine or proteins).

Examples of buffer include sodium acetate, sodium carbonate, citrate, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof.

Examples of preservative in the composition comprising insulin include those of conventional insulin compositions, such as phenol, m-cresol, methylparaben, and zinc or other ions.

In one embodiment, the present disclosure further comprises, in the methods, compositions and combinations described herein, a therapeutically effective amount of at least one or more useful therapeutic agents. Examples of such agents include sulfonylureas, meglitinides, biguanides, thiazolidinediones, dipeptidyl peptidase-4 inhibitors, glucagon-like peptide analogs, gastric inhibitory peptide analogs, and inhibitor of renal sodium-dependent glucose cotransporters.

It will be clear to a person of ordinary skill that if a further additional therapeutic agent is required or desired, ratios will be readily adjusted. It will be understood that the scope of combinations described herein is not particularly limited, but includes in principle any therapeutic agent useful for the prevention and treatment of diseases and conditions related to diabetes described herein.

Pharmaceutical compositions and combinations suitable for use herein may be presented as a solution, a suspension or as an emulsion. The compositions and combinations may be presented in unit dose form in ampoules, bottles, vials, pre-filled syringes, multi-needles, microneedles, etc. and any other tool for subcutaneous injection. Further description of methods suitable for use in preparing pharmaceutical compositions and combinations of the present disclosure and of ingredients suitable for use in said compositions and combinations is provided in *Remington's Pharmaceutical Sciences*, 18(th) edition, edited by A. R. Gennaro, Mack Publishing Co., 1990. The subcutaneous administration of the vasoactive agent and said insulin can be done by means of a syringe, including a pen-like syringe, an infusion pump or transdermal administration (such as by needle-free injection, microneedles, and/or from a patch).

In any embodiment of the methods, composition or combination herein described, said vasoactive agent(s) and insulin(s) are in a combined dosage form.

In any embodiment of the methods, composition or combination the subcutaneous administration of the vasoactive agent and said insulin is by means of a syringe, an infusion pump or by transdermal administration.

In an embodiment, said composition and combination defined herein are for use in any method defined herein, in particular the treatment of diabetes in a subject in need thereof.

EXAMPLES

Patient Recruitment and Inclusion

The OT2D subjects were recruited among CHUS endocrinologists' patients. Healthy subjects were recruited via media. All of the recruited subjects arrived in the morning with an empty stomach (visit 0) to record medical history, to carry out blood and urine samples, to measure the height, the weight, the waist and the body composition (bioelectric impedance, TANITA Corp., United States).

The inclusion criteria for subjects with T2D were: males and females, 18 to 75 years of age, BMI≥30 kg/m², under insulin, $A_{1c}$<10%, non-smoker and <2 alcoholic consumptions/day. We excluded: subjects under the analogue of glucagon-like peptide 1, under dipeptidyl peptidase-4 inhibitor, with hepatic or renal function anomalies (glomerular filtration rate—GFR<50 ml/min), with an unstable thyroid function or abnormal blood and/or urinary tests. Since we were recruiting T2D subjects, the fasting blood glucose, $A_{1c}$ and the lipid profile could be abnormal.

The recruitment criteria for the control healthy normal weight subjects were: males and females, 18 to 75 years of age, BMI>18.5 and <25 kg/m², non-smoker and <2 alcoholic consumptions/day. We excluded: subjects who did intense physical activity on a regular basis, those with abnormal hepatic, cardiac and renal functions, those with an unstable thyroid or abnormal urinary/blood tests, those with a history of gestational diabetes or a family history of T2D to the first degree.

Statistical Analysis of Patient Clinical Profiles

OT2D subjects were different from normal weight subjects for all parameters, except for gender (Table 2). ODT2 subjects were representative of patients with T2D commonly treated by physicians and endocrinologists: obese, over 60 year's old, taking insulin, taking medications (which explains their low mean LDL level), and with an $A_{1c}$ value over the recommended target of 7%.

TABLE 2

Characteristics of subjects involved in our experiments.

| Characteristics | Units | Normal Weight | OT2D |
| --- | --- | --- | --- |
| Gender | MT | 4/2 | 12/4 |
| Age | yrs | 51.5 ± 14.1 | 63.6 ± 9.9* |
| Weight | kg | 60.3 ± 7.3 | 115.2 ± 23.14*** |
| BMI | kg/m² | 22.0 ± 1.8 | 40.6 ± 7.2*** |
| Fat mass | % | 19.4 ± 5.3 | 42.1 ± 10.7*** |
| Waist circumference | cm | 76.8 ± 8.2 | 127.9 ± 13.2*** |
| $A_{1c}$ | % | 5.6 ± 0.4 | 7.9 ± 1.2*** |
| HDL | mmol/l | 1.62 ± 0.29 | 0.97 ± 0.26*** |
| LDL | mmol/l | 2.69 ± 0.72 | 1.59 ± 0.56* |
| Triglycerides | mmol/l | 0.94 ±0.45 | 1.91 ± 1.26* |
| Insulin | U/day | — | 131 ± 76 |
| T2D duration | yrs | — | 18.7 ± 3.8 |

Means ± SD;
*compared to Normal Weight subjects;
*p < 0.05;
***p < 0.001;
exact Fisher test and Mann-Whitney test.

Pre-dosing Instructions to Patients

A 2-day menu was chosen based on the basal metabolic rate given by the bioelectric impedance device and the physical activity habits of the subjects. All of the subjects were given instructions to follow this menu, to not consume alcohol or coffee and to do vigorous exercise during the 48 hours prior to an experimental visit. The volunteers also could not modify their lifestyle between visits of the research project.

Experimental Protocol for Assessment of ATBF

Each volunteer participated in experimental visits at a 2-month interval (radioprotection rules). The technique used was the $^{133}$Xe wash-out technique coupled with a microinjection of a vasoactive agent or vehicle (saline solution) dose (Martin, E. et al. *Can J Physiol Pharmacol* 2011; 89(6):383-91; Sotornik, R. et al. *Methods Enzymol.* 2014; 537:227-42). During an experiment, four measurement sites of ATBF were evaluated simultaneously on the abdomen: two over and two under the navel, to the left and to the right of the navel. Therefore, a site above and a site below can both receive a vasoactive agent dose and both contralateral sites of the saline solution. Each subject is therefore his own control.

The morning of an experiment, the subjects arrived fasting with their dietary report. The weight and body composition were measured once again. The rest of the experiment was conducted in a lying position. Four subcutaneous microcatheters (Quick-Set infusion set, Medtronic Canada Ltée.) were inserted in the abdomen at each of the 4 measurement sites of ATBF. The micro-cateters were 6 mm for the normal weight subjects and 9 mm for the OT2D subjects. They allowed the injection of a radioactive tracer ($^{133}$Xe) and the vasoactive agent at the same exact location as well as limit the subcutaneous tissue lesions. Their insertion is practically painless. Thereafter, 1 to 2 MBq of $^{133}$Xe (Lantheus Medical Imaging, Canada) dissolved in a saline solution to 4° C. was injected at each of the measurement sites. Sixty min were allotted to the equilibration of the $^{133}$Xe in the tissue in order to obtain stable readings. The recording of the data was done with the help of probes detecting the gamma radiations (gamma-counter probe CsI(Tl) scintillator detector, John Caunt Scientific Ltd, Oxford, UK).

An ATBF value is obtained at each 10 min block of reading. The disappearance of $^{133}$Xe is reflected in the decrease in quantity of the gamma emissions which is cumulated every 20 sec. The negative slope of the time every 10 min is therefore converted to an ATBF value (ml/100 g tissuemin) (see Karpe, F. et al. *J Physiol* 2002; 540(Pt 3):1087-93; Martin, E. et al. *Can J Physiol Pharmacol* 2011;89(6): 383-91; Sotornik, R. et al. *Methods Enzymol.* 2014; 537:227-42).

Assessment of ATBF Following Administration of Iloprost, Papaverine, Isoproterenol and Sildenafil Six normal weight subjects and 17 OT2D subjects participated in these experiments. In order to measure the reactivity of ATBF, we administered 3 doses (increasing concentrations) to a same experimental site. Each experiment began with a 60 min reading of ATBF while fasting and without stimulation to calculate the base of the ATBF (ATBF$_b$). Then, a dose of vasoactive agent or saline (100 μl) was injected (bolus) and the ATBF was recorded for 40 min. This volume (100 μl) corresponds to the one of 10 U of insulin. This procedure was repeated for each of the administered doses; about 5 min was necessary for manipulations between the three recording phases. In order to measure the ATBF reactivity duration, OT2D subjects participated to experiments in which one vasoactive agent dose or saline was injected as a volume of 300 μl (corresponding to the volume of 30 U of insulin) and the ATBF was recorded for 120 min.

Figure 1:
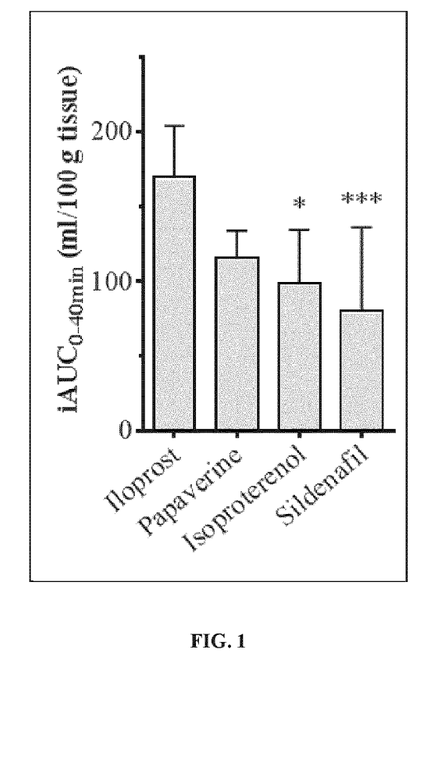
FIGS. 1 and 2 represent the area under the curve observed for subcutaneous adipose tissue blood flow (ATBF) in obese subjects with T2D (ODT2) following the subcutaneous administration of iloprost, papaverine, isoproterenol and sildenafil.

FIG. 1 represents the ATBF from 0-40 min in OT2D subjects (n=8 or 9) observed following the subcutaneous administration of iloprost, papaverine, isoproterenol or sildenafil. Each result (n) corresponds to the incremental area under the curve (iAUC) of the 40-min post-injection ATBF monitoring period for the more effective dose of each vasoactive agent in 100 μl: iloprost 1 umol, papaverine 8.65 μmol isoproterenol 10 umol, and sildenafil 100 nmol. Means±standard deviations (SD); *compared to iloprost; *p<0.05; **p<0.01; Kruskal-Wallis test followed by Dunn's multiple comparisons, p value adjusted for 6 comparisons.

Figure 2:
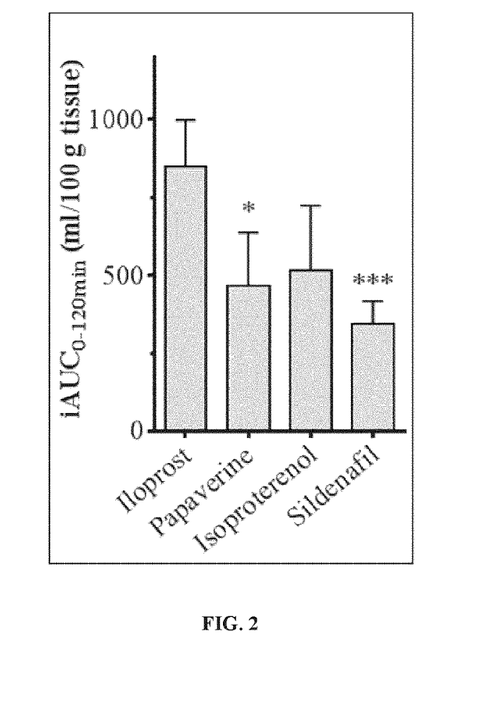

FIG. 2 represents the ATBF from 0-120 min of OT2D subjects (n=7 to 9) observed following the subcutaneous administration of iloprost, papaverine, isoproterenol or sildenafil. Each result (n) corresponds to the incremental area under the curve (iAUC) of the 120-min post-injection ATBF monitoring period for the more effective dose of each vasoactive agent in 300 μl: iloprost 1 umol, papaverine 8.65 μmol, isoproterenol 10 umol, and sildenafil 100 nmol. Means±SD; *compared to iloprost; *p<0.05; ***p<0.001; Kruskal-Wallis test followed by Dunn's multiple comparisons, p value adjusted for 6 comparisons.

Figure 3:
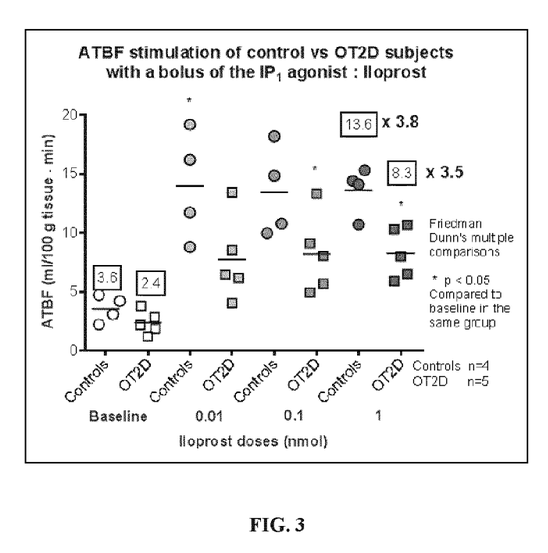
FIG. 3 represents the ATBF in control subjects (circles) and in OT2D subjects (squares) after subcutaneous iloprost administration.

FIG. 3 represents the ATBF in control normal weight subjects (circles) and OT2D subjects (squares) after subcutaneous iloprost administration. The baseline corresponds to the 1-hour monitoring mean of fasting ATBF. The ATBF under stimulation is express as the mean of the 3 higher values. Three incremental doses of iloprost have been applied (0.01, 0.1 and 1 nmol) and the effects on ATBF were monitored over 40-min periods. Group's means are indicated in boxes and fold increase factors of stimulated ATBF are compared to unstimulated ATBF.

Figure 4:
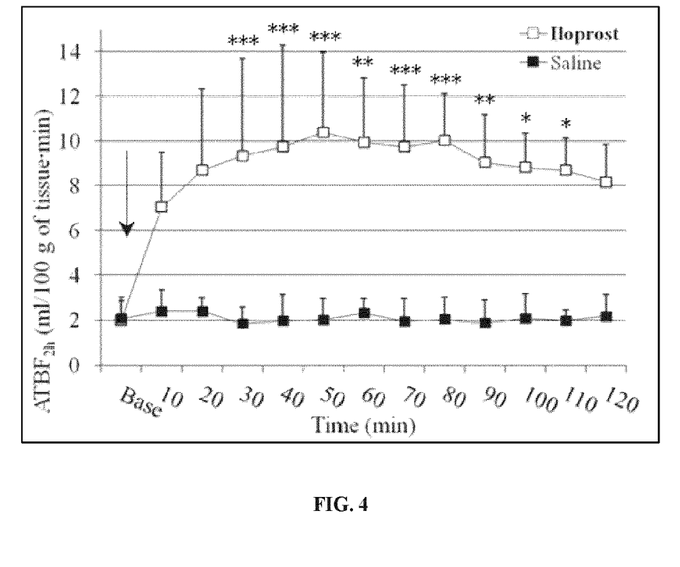
FIG. 4 represents the ATBF in control subjects and OT2D subjects after subcutaneous iloprost administration.

FIG. 4 represents the ATBF in OT2D subjects (n=9) at two 120-min recording sites: after subcutaneous administration of 1 nmol of iloprost (white squares) or of saline (black squares). The baseline corresponds to the 1-hour monitoring mean of fasting ATBF. The black arrow corresponds to the injection time (t=0). Means±SD; *compared to saline; *p<0.05; p<0.01; *p<0.001; Friedman test followed by Dunn's multiple comparisons, p value adjusted for 13 comparisons.

Statistical Method and Analysis

The ATBF$_b$ represents the average of the 3 last values (before 0) out of the 6 obtained during the one-hour basal measurement because they are the most stable. For the dose-response study, the response of ATBF to a vasoactive agent (ATBF$_{max}$) represented the average of the last 3 consecutive highest points out of the 4 values obtained. The multiplication factor of a vasoactive agent corresponds to the ratio ATBF$_{max}$/ATBF$_b$.

The AUC were calculated by the trapezoidal method: the iAUC (incremental USC) of the response to a vasoactive agent was calculated from the values of ATBF minus the ATBF$_b$ for the dose-response test (iAUC$_{0-40min}$) or the tests of 120 min (iAUC$_{0-120min}$)

All of the data is expressed in means±SD. The significance of the nominal variables were calculated with the Fisher's Exact Test. The significance of continuous dependant variables was calculated with the Friedman test followed by Dunn's multiple comparisons, with values of p adjusted for the number of comparisons. The significance of the continuous independent variables was calculated with the Kruskal-Wallis test followed by Dunn's multiple comparisons test, with values of p adjusted for the number of comparisons (GraphPad Prism®, version 6.02). A value of p<0.05 is considered to be significant.

Experimental Protocol for Assessment of SAIA Absorption

Euglycemic clamp. Subjects were admitted to the Sherbrooke University Hospital Clinical Research Center (CRC) at 8 PM the evening prior to each study. An i.v. antecubital cannula was installed to allow venous sampling for immediate whole blood glucose level measurements by a glucose analyzer (FreeStlyle Lite Glucometer, Abbott Diabetes Care Inc.) at 30-min intervals until glycemic target is reached and at 2-hour intervals thereafter. A second contralateral cannula was installed for continuous i.v. administration of regular insulin and glucose, as needed, and plasma glucose has been brought progressively into the normal target range of 5-7 mmol/L overnight and then kept at this level. Experiments started around 8 AM. Patients have been kept fasting (drinking water permitted) during the entire 8-hour clamp study. Another venous catheter was inserted in the hand of sampling limb for arterialized blood sampling, the hand kept warm in a heating pad. After two baseline measurements, 20 min after stopping the overnight regular i.v. insulin infusion (for disappearance of regular insulin from blood), a euglycemic clamp (glucose clamped within a 0.5 mmol/L interval, comprised between 5.0 to 6.5 mmol/L) was performed following sc injection of 10 or 30 U of lispro f iloprost. Plasma glucose levels were monitored every 5 min for the first 4 hours and at 10-min intervals thereafter. Glucose infusion rates have then been adjusted accordingly. Blood samples (2 ml) for specific determination of lispro were collected at 10-min intervals for the first 3 hours, and at 20-min intervals thereafter, in tubes containing sodium-citrate and a cocktail of protease inhibitors. Samples were then immediately centrifuged, frozen in liquid nitrogen and stored at −80° C. until assayed. Study procedures ended around 4 PM. Subjects received a meal and self-injected a personalised insulin dose as prescribed by the endocrinologist. Subjects were allowed to leave when glucose levels were stabilised over 6 mmol/L. Plasma lispro was measured by an ultra-specific radioimmunoassay (Linco Research Inc.) Detection limit is 18 pmol/L, intra-assay CV is 2.5% in our hands (Gagnon-Auger M, et al. Diabetes Care 2010;33 (12):2502-7).

Effects of Adding a Vasoactive Agent on the Absorption of SAIA

OT2D subjects participated to these experiments in which 10 and 30 U of lispro±iloprost were tested. PK profiles were obtained from blood samples collected during the 8-hour euglycemic clamp. PD profiles arc the glucose infusion rates needed to maintain plasma glucose levels stable and correspond to the hypoglycemic effect of insulin.

Figure 5:
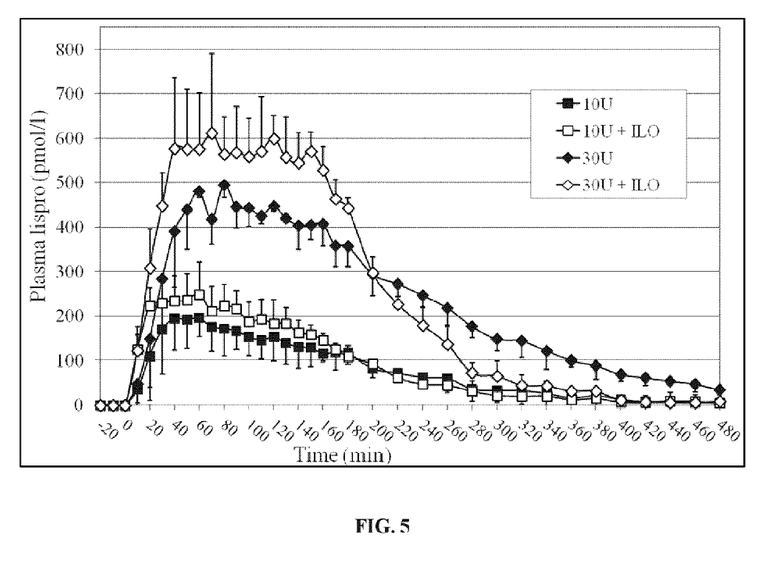
FIG. 5 represents the mean plasmatic lispro concentrations over the 8-hour euglycemic clamp following its administration in OT2D subjects.

FIG. 5 represents the mean plasmatic lispro concentrations over the 8-hour euglycemic clamp following its administration in OT2D subjects with a $A_{1c}$>8%. The SAIA lispro was subcutaneously injected (t=0), at doses of 10 U (n=4) or 30 U (n=3) and with or without 1 nmol of iloprost. Means±SD; $A_{1c}$, glycated hemoglobin; ILO, iloprost; U, insulin units.

Figure 6:
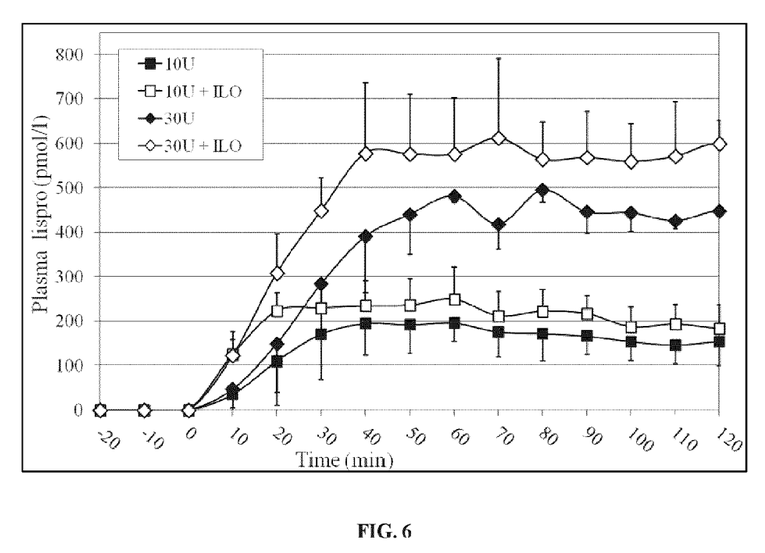
FIG. 6 represents the mean plasmatic lispro concentrations over the first 2-hour of the 8-hour euglycemic clamp following its administration in OT2D subjects.

FIG. 6 represents the 2 first hours of mean plasmatic lispro concentrations of the 8-hour euglycemic clamp following its administration in OT2D subjects with a $A_{1c}$>8%. The SAIA lispro was subcutaneously injected (t=0), at doses of 10 U (n=4) or 30 U (n=3) and with or without 1 nmol of iloprost. Means±SD; $A_{1c}$, glycated hemoglobin; ILO, iloprost; U, insulin units.

Figure 7:
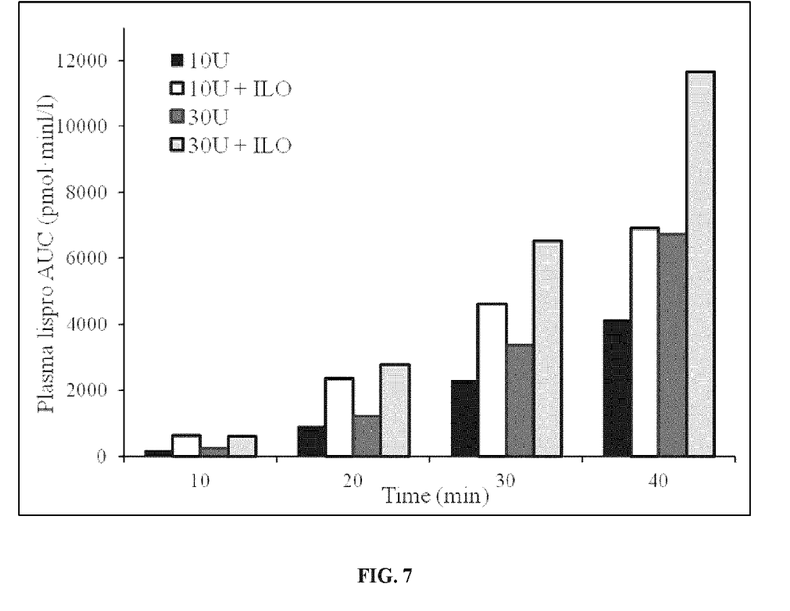
FIG. 7 represents fractional AUCs of plasmatic lispro concentrations at the early absorption phase (10 to 40 min) of the 8-hour euglycemic clamp following its administration in OT2D subjects.

FIG. 7 represents fractional AUCs of plasmatic lispro concentrations at 10, 20, 30, and 40 min following its administration in OT2D subjects with a $A_{1c}$>8%. The SAIA lispro was subcutaneously injected (t=0), at doses of 10 U (n=4) or 30 U (n=3) and with or without 1 nmol of iloprost. Means; $A_{1c}$, glycated hemoglobin; AUC, area under the curve; ILO, iloprost; U, insulin units.

Figure 8:
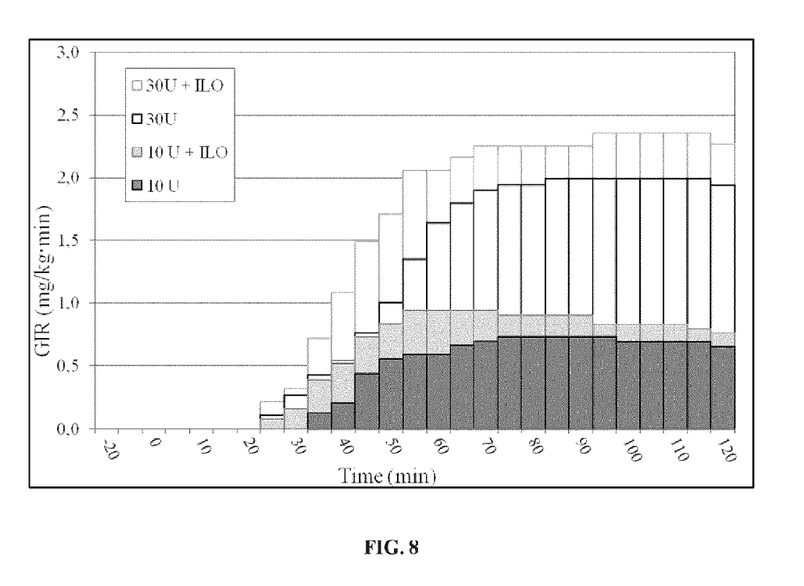
FIG. 8 represents the glucose infusion rate over the first 2-hour of the 8-hour euglycemic clamp following lispro administration in OT2D subjects.

FIG. 8 represents the 2 first hours of mean glucose infusion rate of the 8-hour euglycemic clamp following lispro administration in OT2D subjects with a $A_{1c}$>8%. The SAIA lispro was subcutaneously injected (t=0), at doses of 10 or 30 U and with or without 1 nmol of iloprost. Means; $A_{1c}$, glycated hemoglobin; GIR, glucose infusion rate; ILO, iloprost; U, insulin units.

Figure 9:
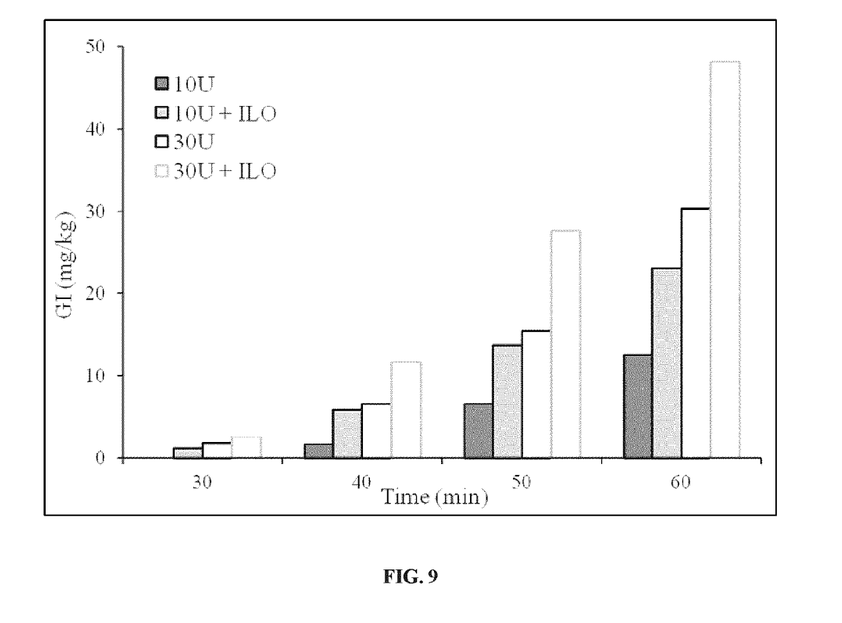
FIG. 9 represents the total glucose infusion at the early action phase (30 to 60 min) of the 8-hour euglycemic clamp following lispro administration in OT2D subjects.

FIG. 9 represents the total glucose infusion at 30, 40, 50, and 60 min following lispro administration in OT2D subjects with a $A_{1c}$>8%. The SAIA lispro was subcutaneously injected (t=0), at doses of 10 or 30 U and with or without 1 nmol of iloprost. Means; $A_{1c}$, glycated hemoglobin; GI, glucose infusion; ILO, iloprost; U, insulin units.

Statistical Method and Analysis

The fractional plasmatic lispro AUCs were calculated by the trapezoidal method. Total glucose infusion (GI) is obtained by multiplying the glucose infusion rate (GIR) by the time (min). All of the data is expressed in means.

To conclude, maximal plasma lispro concentrations and maximal glucose infusion rates were both rapidly increased with the addition of iloprost (FIGS. 5 and 8). Both lispro absorption and hypoglycemic effect were accelerated by iloprost in regard to fractional AUCs and early total glucose infusion (FIGS. 7 and 9). Altogether, these data suggest that 1) the ATBF is increased pharmacologically with specific vasoactive agents not only in normal subjects but also in insulin resistant OT2D patients, and 2) the simultaneous administration of a vasoactive agent (capable of increasing ATBF at the injection site) and insulin accelerates the subcutaneous absorption and effectiveness of the latter with no side effects in insulin resistant OT2D patients. These findings provide clinical proof-of-concept for the effectiveness of combining a specific vasoactive agent to insulin (or its analogs) in order to enhance its pharmacokinetic (absorption) and pharmacodynamic activity (hypoglycemic action) in patients under insulin therapy. Moreover, because of the fast onset of action of the combination of insulin(s) with vasoactive agent(s), it may be more effective at reducing postprandial hyperglyceamic peaks and ensuing diabetes complications, which arc of major clinical importance.

While the disclosure has been described in connection with specific embodiments thereof, it is understood that it is capable of further modifications and that this application is intended to cover any variation, use, or adaptation of the disclosure following, in general, the principles of the disclosure and including such departures from the present disclosure that come within known, or customary practice within the art to which the disclosure pertains and as may be applied to the essential features hereinbefore set forth.

The invention claimed is:

1. A method for treating diabetes comprising simultaneously administering subcutaneously to the same site in a subject in need thereof, a therapeutically effective amount of a short-acting insulin analog (SAIA) and a subcutaneously vasoactive effective amount of iloprost; wherein the ratio of SAIA to iloprost is 10-30 U SAIA: about 1 nmol iloprost; wherein the vasoactive effective amount of iloprost causes a local increase of blood flow in subcutaneous adipose tissue.

2. The method of claim 1, wherein the SAIA is insulin lispro, insulin glulisine or insulin aspart.

3. The method of claim 2, wherein said subject is a human Type 2 diabetes (T2D) patient.

4. The method of claim 3, wherein said subject is an obese human Type 2 diabetes (T2D) patient.

5. The method of claim 3 further comprising administering a therapeutically effective amount of at least one or more therapeutic that is a sulfonylurea, a meglitinide, abiguanide, a thiazolidinedione, a dipeptidyl peptidase-4 inhibitor, a glucagon-like peptide analog, a gastric inhibitory peptide analog, an inhibitor of renal sodium-dependent glucose cotransporters, or a combination thereof.

6. The method of claim 3, wherein the SAIA and the iloprost are comprised in a single composition when they are administered to the subject.

7. The method of claim 6, wherein the composition is administered subcutaneously with a syringe or an infusion pump.

8. The method of claim 7, wherein the method increases subcutaneous absorption of the SAIA as compared to administration of the same SAIA without iloprost.

* * * * *